United States Patent [19]

Hui et al.

[11] Patent Number: 4,900,855

[45] Date of Patent: Feb. 13, 1990

[54] CHEMICAL PROCESS FOR OBTAINING HIGH PURIFICATION OF MONOALKYLARSINES AND DIALKYLARSINES AND PURIFIED MONO- AND DIALKYLARSINES

[75] Inventors: Benjamin C. Hui, Peabody; Ravindra K. Kanjolia, North Andover, both of Mass.; Jorg Lorberth, Niederweimar, Fed. Rep. of Germany

[73] Assignee: CVD Incorporated, Woburn, Mass.

[21] Appl. No.: 284,000

[22] Filed: Dec. 14, 1988

[51] Int. Cl.$^4$ ............................. C07F 9/70; C07F 9/72
[52] U.S. Cl. ......................................... 556/70; 556/71
[58] Field of Search ..................................... 556/71, 70

[56] References Cited

U.S. PATENT DOCUMENTS 1,313,657  8/1919  White ..................................... 556/70

OTHER PUBLICATIONS

Phillips et al., *Canadian Journal of Chemistry*, 45, 675 (1967).

*Primary Examiner*—Paul F. Shaver
*Attorney, Agent, or Firm*—Wayne E. Nacker; Gerald K. White

[57] ABSTRACT

A method is provided for highly pure mono- and dialkylarsines, particularly removing substantially all silicon-containing impurities. A mono- or dialkylarsine is reacted with either an alkali metal or an alkali metal hydrocarbyl, thereby producing an alkali metal alkylarsenide. Silicon, germanium, zinc and other metallic impurities are removed from the alkali alkylarsenide. Mono- and dialkylarsine is then regenerated by reaction of the alkali metal alkylarsenide with a proton donor.

7 Claims, No Drawings

4,900,855

CHEMICAL PROCESS FOR OBTAINING HIGH PURIFICATION OF MONOALKYLARSINES AND DIALKYLARSINES AND PURIFIED MONO- AND DIALKYLARSINES

The present invention is directed to a method of purifying mono- and dialkylarsines to very high purity, whereby the purified alkylarsines are suitable for chemical vapor deposition (CVD) or other processes which require mono- and dialkylarsines of very high purity.

BACKGROUND OF THE INVENTION

Gallium arsenide (GaAs), a III-V compound, is a material which has important specific optical and electronic applications. GaAs films are currently formed by chemical vapor deposition from the decomposition of an arsenic-containing compound and a gallium-containing compound. The arsenic-containing compound commonly used for forming gallium arsenic film is arsine, $AsH_3$. $AsH_3$ is highly toxic, the TLV in air of $AsH_3$ being 0.05 ppm. Furthermore, it is a gas, the compound having a boiling point of $-62.5°$ C. Accordingly, it must be handled with extreme caution. The hazard presented by $AsH_3$ is such that contemplated regulations proscribe its industrial use in the U.S. Finding a less hazardous substance than arsine, which may be used to deposit arsenic-containing films, is highly desirable, and may be absolutely necessary should the use of arsine be banned.

Potential alternatives for arsine itself are organoarsines. Although mono- and dialkylarsines are toxic, they are less so than arsine. Importantly, they are generally liquid or solid at room temperature, making them far safer to handle than arsine. Both diethylarsine, $Et_2AsH$, and mono tertiary butylarsine, $t\text{-}BuAsH_2$, have been used as alternate arsenic sources with some degree of success. Diethylarsine is a liquid at room temperature and has a boiling point of 105° C. Mono t-butylarsine is also a liquid with a boiling point of 65°–67° C. Other alkylarsines have sufficiently low boiling or sublimation points that they may be vaporized at combinations of temperature and pressure consistent with chemical vapor deposition.

A hindrance to the use of mono- and dialkylarsine for CVD or other deposition processes is the difficulty in purifying such compounds, particularly with respect to levels of silicon-, zinc- and germanium-containing compounds. Using currently available synthetic techniques and purification methods, mono- and dialkylarsines can generally achieve at best a level of silicon as low as about 200 to 300 ppm. For producing GaAs films useful for electronic purposes, an arsenic-containing compound having a silicon level of less than 5 ppm, and preferably less than 1 ppm, must be used. Trace levels of silicon are known to seriously impair the optical and electrical qualities of GaAs films. Applicants have found, for example, that fractional distillation of diethylarsine in a three-foot stainless steel packed column is inadequate to rid the compound of silicon impurities.

It is a general object of the present invention to provide methods of highly purifying mono- and dialkylarsines, particularly to substantially remove all trace silicon-containing, zinc-containing and germanium-containing impurities from the primary and secondary arsines.

SUMMARY OF THE INVENTION

In accordance with the method of the invention, a monoalkylarsine or a dialkylarsine is reacted with either an alkali metal or an alkali metal hydrocarbyl, thereby producing an alkali metal alkylarsenide compound. Alkali mono- or dialkylarsenides are solid. Metal impurities are removed from the solid alkali metal arsenide compounds by washing with appropriate solvent and/or drying in vacuo. The mono- or dialkylarsine may then be regenerated with a proton donor compound, e.g., an acid, an alcohol, or even water.

DETAILED DESCRIPTION OF CERTAIN PREFERRED EMBODIMENTS

The purification method of the present invention is based upon the reaction of liquid alkylarsines with a reagent that produces a solid compound from which associated silicon-containing, zinc-containing and germanium-containing and other impurities may be easily removed, removing these impurities from the solid compound and then regenerating the alkylarsines.

In accordance with the method of the present invention, a monoalkylarsine or a dialkylarsine is reacted with either an alkali metal, such as metallic lithium, or an alkali metal hydrocarbyl, such as butyl lithium, thereby producing an alkali metal alkylarsenide. The metal-containing impurities are generally non-reactive with either the alkali metal or the alkali metal hydrocarbyl. Whereas, the liquid alkylarsines are difficult to purify with respect to these metallic impurities, the solid alkali metal alkylarsenides may be relatively easily separated from the metallic impurities. Such methods include washing with organic solvents, recrystallization in organic solvents, drying in vacuo for extended periods of time, and combinations of these methods, depending on the degree of purity required. Subsequent to purification of the solid alkali alkylarsenides, these compounds are reconverted to alkylarsines using a proton donor compound, e.g., an acid, an alcohol, or water. The by-product of this reconversion step is an alkali metal salt, -alkoxide or -hydroxide which may be easily separated from the alkylarsines.

For purposes of this invention, primary and secondary alkylarsines have the formula $RAsH_2$ and $R_2AsH$ where the R or R's are alkyl moieties which are the same or different and each have between 1 and 5 carbon atoms. The R's may be straight chain or branched. The alkylarsines presently considered most useful for chemical vapor deposition are diethylarsine, $Et_2AsH$ and mono tertiary butylarsine, $t\text{-}BuAsH_2$. Dimethylarsine, $Me_2AsH$, and monoethylarsine, $EtAsH_2$ are other useful compounds, although their low boiling points may increase their hazardous potential.

The alkali metal, herein designated M, employed either in metallic form or as an alkali metal hydrocarbyl, is any of the metals of Group IA of the periodic table; however, the lower molecular weight metals, i.e., Li, Na and K, or a mixture of these will generally be used. In the alkali metal hydrocarbyls, herein designated as $MR'$, the hydrocarbyl ($R'$) group is broadly defined herein as any hydrocarbon radical which forms an organometallic compound with Group IA metals. The preferred hydrocarbyl species are alkyl groups, especially lower alkyl groups (defined as those having from one to four carbon atoms). Specifically, all isomers of methyl, ethyl, propyl, and butyl moieties are contemplated hydrocarbyl species. Other, exemplary hydrocarbyl moieties are saturated or unsaturated cycloalkyl, preferably having from about 5 to about 12 carbon atoms, most preferably cyclopentadienyl; aryl, preferably phenyl. Preferably, R' is selected so that HR' is either a gas or a low boiling liquid, whereby HR' is readily removed from the alkylarsenide in this step.

Reactions (I, II) between the alkylarsine and the metal and (III & IV) between the alkylarsine and the metal hydrocarbyl are as follows:

$$2R_2AsH + 2M \rightarrow 2R_2AsM + H_2 \qquad (I)$$

$$RAsH_2 + 2M \rightarrow RAsM_2 + H_2 \qquad (II)$$

$$R_2AsH + R'M \rightarrow R_2AsM + R'H. \qquad (III)$$

$$RAsH_2 + 2R'M \rightarrow RAsM_2 + 2R'M. \qquad (IV)$$

Importantly, whereas the mono- and dialkylarsines are generally liquid at room temperature, the alkali metal alkylarsenides ($R_2AsM$, $RAsM_2$) compounds are generally solid at room temperature. Furthermore, the silicon-containing and other metal-containing impurities are generally non-reactive with either the alkali metal or the alkali metal hydrocarbyl, and the $R_2AsM$ and $RAsM_2$ compounds are readily separable from the silicon-containing impurities by a variety of methods. In the event, where silicon-containing impurities species react with alkali metal or alkali metal hydrocarbyl to form a non-volatile solid, the next step of regeneration does the separation.

Reactions (I) through (IV) are carried out in an organic solvent which is free of proton sources (water and alcohols, for example, are unacceptable). The solvent system should dissolve the alkylarsine, and in Reaction (III) and (IV), preferably dissolves the alkali metal hydrocarbyl. One suitable solvent system is ether/hexane in which the alkylarsine and the alkali metal hydrocarbyl of Reactions (III, IV) are mutually soluble. For Reaction (I) and (II), a solution of the alkylarsine is contacted with the alkali metal.

The $RAsM_2$ and $R_2AsM$ compounds may precipitate from the solution or may be obtained from the solution by evaporating the solvent. The product R'H is either a gas at room temperature or has a sufficiently high vapor pressure to be removed from $RAsM_2$ or $R_2AsM$ by heating. The $RAsM_2$ or $R_2AsM$ solid may be partially purified, particularly with respect to silicon impurities, by washing with organic solvent. Recrystallization in organic solvent is another method of reducing impurities in the alkali metal alkylarsenide.

The step considered most critical for removing silicon-containing, zinc-containing and germanium-containing impurities from $RAsM_2$ and $R_2AsM$ compounds is vaporization of the impurities. Silicon, zinc and germanium impurities tend to have relatively high vapor pressures relative to $RAsM_2$ and $R_2AsM$ compounds; thus, purification may be achieved by subjecting these compounds to heat and/or vacuum for suitable periods of time. Removal of silicon, zinc and germanium impurities to achieve silicon, zinc and germanium levels below 5 ppm requires the application of heat and/or vacuum to the $RAsM_2$ or $R_2AsM$ compounds. The amount of impurities removed depends upon the combination of temperature, vacuum and time. To achieve any practical rate or impurity removal it is felt that a vacuum of at least about 20 torr should be applied, and higher vacuums, such as 0.01 torr are preferred. If a high enough vacuum is applied, impurity removal can be achieved at ambient temperatures; however, mild heating, e.g., to 40° C. and above, enhances the rate of impurity removal. Care must be taken, however, that a temperature is not reached whereat the $RAsM_2$ or $R_2AsM$ compound decomposes, and it is preferred that the temperature for removal of impurities be maintained below about 70° C.

A combination of purification methods is typically used to achieve a desired degree of purity; for example, washing with organic solvent followed by exposure to vacuum.

Next, the alkylarsine is regenerated by reacting the $RAsM_2$ or $R_2AsM$ compound with a proton-donor according to Reaction (V) and (VI):

$$RAsM_2 + 2H^+ \rightarrow RAsH_2 + 2M^+ \qquad (V)$$

$$R_2AsM + H^+ \rightarrow R_2AsH + M^+ \qquad (VI)$$

The proton-donor may be practically any compound which provides a proton, such as an acid; providing that the proton donor is separable from the alkylarsine and does not contaminate it. Suitable representative acids, include the halogen acids (HX where X is a halogen), sulfonic acid, and a variety of organic acids, such as acetic acid. Even weaker proton donors, such as water and alcohols, will effect Reaction (V and VI). Typically, the alkylarsenide compounds will be dissolved or suspended in an organic solvent, e.g., ether, and exposed to a predetermined amount of a proton donor therein, e.g., by bubbling HCl through the solvent or addition of water or alcohol. Preferably, the proton donor selected will be easily separable from the alkylarsine. HCl, for example, will produce MCl which will immediately precipitate from the solution containing the alkylarsine. Any other halogen acid having the formula HX, X being a halogen, may be used for this purpose as well. The solvent and the volatile alkylarsine is transferred in-vacuo to leave a solid residue. The solvent is then removed to obtain pure alkylarsine. The use of alcohol or water is preferred for regeneration as they form non-volatile, LiOH, LiOR and Si-O-Si species. Oxygen-containing hydrogen donor compounds, such as alcohols and water, are found to help remove non-volatile silicon impurities. Thus, a second step for removing the silicon impurity is introduced.

The method of the present invention purifies $RAsM_2$ and $R_2AsM$ compounds to have levels of silicon, germanium and zinc, each below about 5 ppm. Purifications of these compounds to this level makes these compounds useful in processes, such as CVD, useful for forming films or layers suitable for advanced optical and electronic applications.

The invention will now be described in greater detail by way of specific example.

EXAMPLE 1

The experimental manipulations were carried out in the inert atmosphere. 198 g (1.47 mol) of $Et_2AsH$ (ICP analyses Si=200 ppm, Zn=2 ppm) was taken in a 3 liter three-necked flask fitted with an addition funnel and dry ice condenser. 1.5 liter of n-pentane was added to the reaction flask. 700 ml of n-Bu-Li (2.2M in hexane) was diluted with 300 ml of pentane and was added to the additional funnel. n-BuLi was added dropwise to the solution of $Et_2AsH$ at −78° C. while stirring. The addition was completed in 4 hours, and the mixture was allowed to stand overnight. An off-white fluffy precipitate was noted in the flask. the solvent was removed in-vacuo, and the resultant brown solid was dried in vacuum at 50°-70° for 5 hours. This compound, LiAsEt₂ is extremely air sensitive, and an exothermic reaction takes place in the presence of air.

In the second step of regeneration, 110.0 g (0.78 mol) of Et₂AsLi was suspended in 600 ml of degassed pentane. To this was added 35 ml of methanol in a dropwise manner. The reaction was carried out at room temperature (25° C.). An exothermic reaction took place, and the rate of addition was controlled to maintain a gentle reflux. The reaction mixture was allowed to stir overnight. The volatile contents were transferred in-vacuo via flask-to-flask technique leaving behind a grayish-white solid residue of LiOMe in the reaction flask. Excess pentane and methanol from the distillate were removed by fractional distillation. Pentane/methanol azeotrope distilled at 30° C. The final compound, Et₂AsH, was identified by NMR data and following ICP, trace metal analyses were obtained:

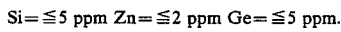

Si=≦5 ppm Zn=≦2 ppm Ge=≦5 ppm.

EXAMPLE 2

8.9 g (0.066 mol) of diethylarsine, Et₂AsH, was dissolved in about 40 ml of diethylether in a 250 ml 3-neck flask. 45 ml of 1.5M n-BuLi in hexane (0.067 mol) was taken in an addition funnel and cooled to −70° C. The reaction flask was chilled to −70° C., and n-BuLi was added to this in a dropwise manner while stirring. With the first droplet instantaneous precipitation occurred indicating insolubility of Et₂AsLi in one of the solvents (hexane). After addition, all volatiles are condensed in vacuo and the solid off-while residue was obtained. This residue was washed with hexane and dried in vacuo at room temperature, and analyzed as Et₂AsLi.

[Analyses %C=34.3 (calcd.), 33.3 (found);
%H=7.15 (calcd.) 7.13 (found)]

Lithium diethylarsenide, Et₂AsLi, obtained above was heated at 50°-70° C. in vacuum for 6 hours. 8.0 g of Et₂AsLi was suspended in 100 ml hexane in a 3-neck 500 ml flask attached with a dry ice condenser and a gas inlet system. The suspension was cooled between −15° and −20° C., and a known quantity of dry HCl is bubbled through. The reaction took place as white lithium chloride quickly formed. The volatile contents of the reaction were condensed in-vacuo into a receiver flask. The distillation of excess hexane left behind pure Et₂AsH. The final product is identified by ¹H NMR spectrum and analyzed by ICP. The reduction in silicon-containing, zinc-containing and germanium-containing impurities was noted.

While the invention has been described in respect to certain preferred embodiments, modifications obvious to one with ordinary skill in the art may be made without departing from the scope of the present invention.

Various features of the invention are set forth in the following claims.

What is claimed is:

1. A method for obtaining a mono- or a dialkylarsine that is highly purified with respect to levels of silicon, germanium and zinc, the method comprising,
    in a non-proton donor organic solvent and in the absence of oxygen, reacting a mono- or dialkylarsine with either an alkali metal or a mixture of alkali metals or an alkali metal hydrocarbyl or mixed alkali metal hydrocarbyl to produce an alkali metal mono- or dialkylarsenide,
    using heat and/or vacuum, removing by vaporization silicon-containing, germanium-containing and zinc-containing impurities,
    in a non-proton donor organic solvent and in the absence of oxygen, regenerating said mono- or dialkylarsine by reacting said alkali metal mono- or dialkylarsenide with a proton donor selected from the group consisting of acids, alcohols and water,
    separating said non-proton donor organic solvent which contains said regenerated mono- or dialkylarsine from any solid residue, and
    removing said solvent from said regenerated mono- or dialkylarsine.

2. A method according to claim 1 wherein said mono- or dialkylarsine is initially reacted with an alkali metal hydrocarbyl or mixed alkali metal hydrocarbyl.

3. A method according to claim 2 wherein said mono- or dialkylarsine is reacted with said alkali metal hydrocarbyl or mixed alkali metal hydrocarbyl in a non-proton donor organic solvent in which said mono- or dialkylarsine and said alkali metal hydrocarbyl or mixed alkali metal hydrocarbyl are mutually soluble.

4. A method according to claim 1 wherein said mono- or dialkylarsine is initially reacted with an alkali metal.

5. A method according to claim 1 wherein said alkali metal or the alkali metal of said alkali metal hydrocarbyl is selected from the group consisting of lithium, potassium, sodium, and mixtures thereof.

6. A method according to claim 1 wherein said mono- or dialkylarsine is regenerated by dissolving said alkali metal mono- or dialkylarsenide in said organic solvent and bubbling therethrough a gas having the formula HX where X is a halogen.

7. A method according to claim 1 wherein said proton donor is water or alcohol.

* * * * *